United States Patent [19]
Kloess et al.

[11] Patent Number: 5,782,842
[45] Date of Patent: Jul. 21, 1998

[54] MEDICAL INSTRUMENT GUIDANCE APPARATUS AND METHOD

[75] Inventors: Wolfgang Kloess; Christian Frahm, both of Luebeck, Germany

[73] Assignee: Daum GmbH, Shwerim, Germany

[21] Appl. No.: 587,240

[22] Filed: Jan. 16, 1996

[30] Foreign Application Priority Data

Jan. 16, 1995 [DE] Germany .................. 195 01 069.8

[51] Int. Cl.$^6$ ........................................ A61B 19/00
[52] U.S. Cl. ............................... 606/130; 378/206
[58] Field of Search .................. 606/130; 128/653.1, 128/754; 356/399; 378/205, 206; 600/476, 478

[56] References Cited

U.S. PATENT DOCUMENTS

| | | |
|---|---|---|
| 3,117,480 | 1/1964 | Peddinghaus ............... 83/520 |
| 4,538,289 | 8/1985 | Scheibengraber ............ 378/206 |
| 4,836,671 | 6/1989 | Bautista ..................... 378/206 |
| 5,662,111 | 9/1997 | Cosman .................... 128/653.1 |

*Primary Examiner*—Robert A. Hafer
*Assistant Examiner*—Justine R. Yu
*Attorney, Agent, or Firm*—Merchant, Gould, Smith, Edell, Welter & Schmidt, P.A.

[57] ABSTRACT

A device for marking a planned guide path of a medical instrument such as a puncture needle is disclosed. The device incorporates two sources of electromagnetic radiation, such as lasers, which produce two light rays. The intersecting line of the light rays marks the guide path for the puncture needle. Deviations of the angle position of the puncture needle from the planned guide path are visible by examining the reflection of the light from the puncture needle. Different colors of light may be used with the light rays being formed in a fan-shape in a common plane. In this manner, the color of the reflected light on the surface of the puncture needle changes depending on whether the puncture needle is located at the intersection of the light rays.

14 Claims, 3 Drawing Sheets

MEDICAL INSTRUMENT GUIDANCE APPARATUS AND METHOD

BACKGROUND OF THE INVENTION

The present invention is directed to a device for marking a guide path for an instrument, and in particular, to a device using intersecting light for marking a guide path for a medical instrument such as a puncture needle or a catheter.

In recent years, a number of medical techniques have been developed which require various parts of the external body as well as internal organs to be punctured for diagnosis and/or therapy. For example, biopsies can be taken using small puncture instruments in a manner such that suppurations or blood effusions can be reduced. In many such techniques a relative small area deep under the skin is to be punctured. In such cases, it is often quite difficult to place the puncture needle safely in the desired area.

In a conventional procedure, sectional images are made using computer tomography (CT) or magnetic resonance imaging (MRI). The physician uses these sectional images to determine the area to be punctured, the most suitable entry point and the puncture path. After an initial image is obtained, for example a tomograph, the patient is removed for the imaging machine and the entry point determined according to the sectional image is marked by a point or a line. After usual disinfection, the patient is draped in sterile fashion and, if necessary, local anesthesia is made. The physician then inserts the puncture needle freehandedly into the patient on the basis of a visual estimate of the desired entry angle.

Once the puncture needle is inserted, the patient is once again placed into the imaging apparatus and a new image is made for use in controlling the needle position in the body. If the insertion angle substantially deviates from the intended approach the planned diagnosis or therapy may not be performed and the instrument must be removed and the puncture has to be repeated.

Conventionally, multiple punctures are often necessary in order to properly access the appropriate area. Moreover, deviations from the planned puncture path may cause complications such as lesions of vessels or nerves as well as hemorrhages or infections. Even a very experienced physician using the conventional technique to visually estimate the puncture angle will make a puncture which deviates from the desired angle on the order of ±5°. This order of deviation limits the use of the puncture techniques to cases where the area to be punctured is large enough to accommodate such deviations. Such deviations also make it very difficult or even impossible to puncture small tumors located deep under the skin. Accordingly, there exists a need to provide a device which permits placement and guidance of such instruments more precisely than current techniques.

SUMMARY OF THE INVENTION

Generally, the present invention provides an improved method and apparatus for inserting a medical instrument along a desired path into part of a body. In one particular embodiment, the present invention is implemented in the form of two sources of electromagnetic radiation producing first and second rays which intersect at the planned guide path to mark the planned guide path for insertion of the medical instrument. Using such an apparatus, the medical instrument can be precisely guided along the guide path at the point of intersection.

The above summary of the present invention is not intended to present each embodiment or every aspect of the present invention. Rather, the invention will be understood by reference to the figures and the associated description which follow.

BRIEF DESCRIPTION OF THE DRAWINGS

The invention may be more completely understood in consideration of the following detailed description of various embodiments of the invention in connection with the accompanying drawings, in which.

Figure 1:
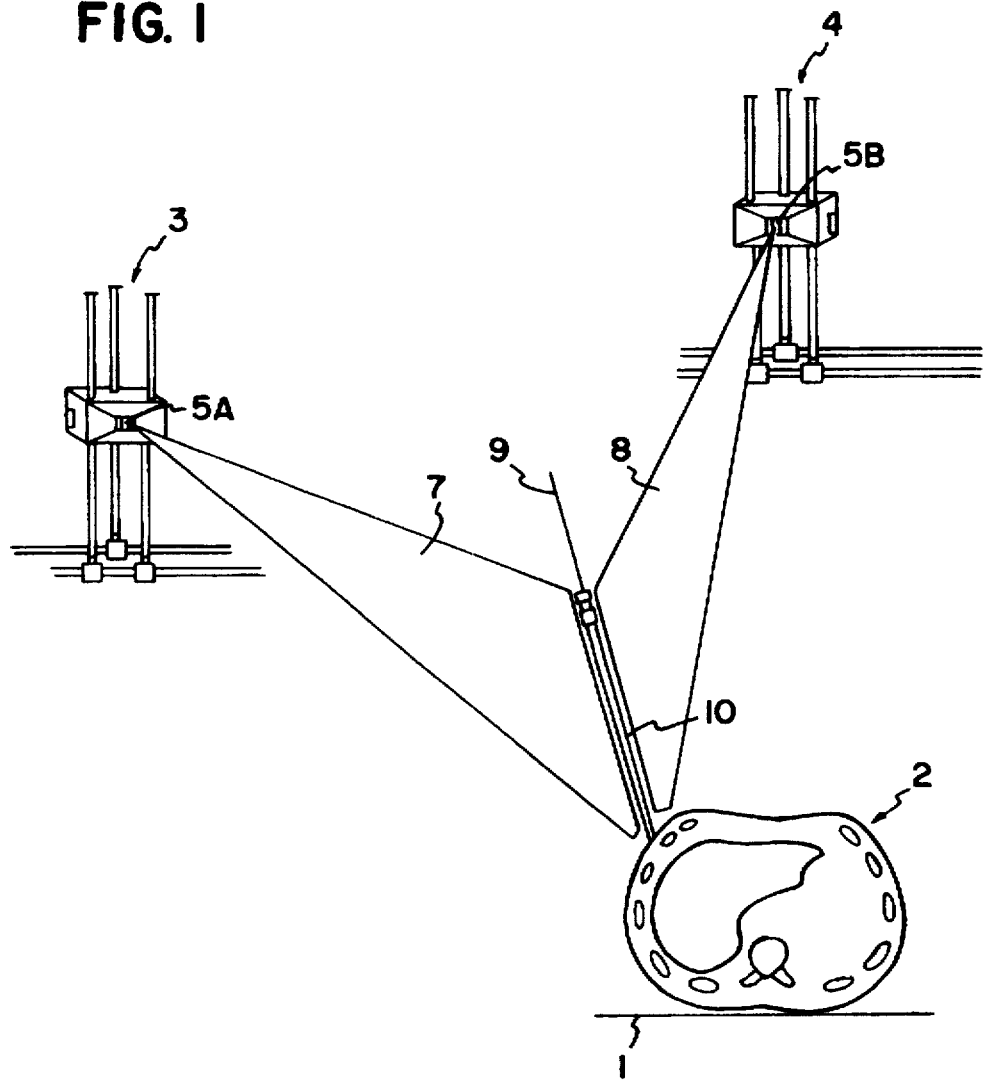
FIG. 1 is a schematic illustration of an embodiment of the invention.

While the invention is amenable to various modifications and alterative forms, specifics thereof have been shown by way of example in the drawings and will be described in detail. It should be understood, however, that the intention is not to limit the invention to the particular embodiment described. On the contrary, the intention is to cover all modifications, equivalents, and alternatives falling within the spirit and scope of the invention as defined by the appended claims.

DETAILED DESCRIPTION

In accordance with an embodiment of the invention, a device is provided for marking a planned guide path for insertion of a medical instrument, such as a puncture needle, into part of a patient's body. At least two sources of electromagnetic radiation are used to mark a guide path for the instrument. The light rays are directed in a manner such that the intersecting point of the light rays marks the planned guide path. In one embodiment, the sources of electromagnetic radiation produce planar rays. The intersecting line of the planes marks the planned guide path. The intersecting angles of the rays are preferably in the range of 60°–120°, and more preferably at an angle of 90°.

In accordance with an embodiment of the invention, the puncture needle is illuminated by the electromagnetic radiation and reflects such radiation. If the puncture needle is situated precisely on the intersecting line of the two rays, that is if the puncture needle is precisely aligned along the planned guide path, it reflects the rays of both sources so that the observed intensity is increased. It is noted that a number of different types of electromagnetic radiation may be used. For example, visible light may be used such that, if the needle is situated in the intersecting line of the two light beams and if it reflects the light of the two sources, the increased intensity of the reflection can be readily determined by visual inspection. In an alternative example, non-visible electromagnetic radiation such ultraviolet radiation which produces a visible reflection can be used. The puncture needle may be coated with materials which emit visible light when radiation at the selected wavelengths are used.

To further facilitate a visual determination of the correspondence of the medical instrument and the intersection point of the light rays, different colors of light may be used. For example, one light source may send red light and the other green light. At the intersecting point of the two light rays the additive mixture of the read and green light causes the production of yellow light. If the puncture needle reflects yellow light, it can be determined that the needle is situated at the planned insertion angle. Deviations from the planned angle of insertion are immediately noticed because a clear red or green coloring will then be reflected by the needle. Using the techniques of the above embodiment, the planned angle of insertion can be observed with deviations less than 1°.

As described more fully below, diode lasers may efficiently be used as light sources. For example, a first diode laser having a wavelength of 532 nm (green light) and a second with having a wavelength of 635 nm (red light) could be used to produce the light rays. Such diode lasers are advantageous in that they not harmful to the eyes of the physician or patient. Light from the diode lasers may be fan-shaped using a cylindrical lens. The two fan-shaped beams mark at their intersecting line the planned puncture path for the puncture needle.

The fan-shaped rays may be spread in only one direction to produce a single light beam. In this manner a relatively well-focussed intersecting line of this rays is formed. This is especially useful when small medical instruments are used such as the puncture needle. If a larger medical instrument is to be guided, or if larger deviations of the insertion angle can be tolerated, it is additionally possible to fan-shape the light rays in a second direction, vertical to the above described beam. In this manner, although not as well focused, the intersecting area of the rays is increased to provide a larger guide path.

As described above, sectional images are used to determine the appropriate guide path. Magnetic resonance imaging is increasingly used instead of the computer tomographic because of the relative high volume of x-rays the patent is subjected to when producing a computer tomographic image. When the device is to be implemented with magnetic resonance imaging, it is desirable to have the entire device constructed of non-magnetic material in order to avoid the influence on the image obtained.

Referring to FIG. 1, a more specific exemplary embodiment in accordance with the invention is illustrated. In FIG. 1, a cross section of an object to be punctured, such as a patient 2, situated on a table 1 is illustrated. More particularly, the cross-sectional view of patient 2 shows a part of the liver which is to be punctured. The table 1 is adjustable in the x- and y-direction, that is in the table plane, in a known manner. The patient 2 is situated on the table 1 in a determined position.

Laser guidance systems 3 and 4 are arranged in a defined position relative to the table 1 and consequently to patient 2. The laser-guidance systems 3 and 4 include diode lasers 5A and 5B, respectively. Diode laser 5A of laser-guidance system 3 outputs a bright red light ray (e.g., at a wavelength of 635 nm) and diode laser 5B of laser guidance system 4 outputs a bright green light ray (e.g., at a wavelength of 532 nm).

The laser rays are fan-shaped by means of cylindrical lenses in one plane in a manner that a bright red fan-shaped ray 7 and a bright green fan-shaped ray 8 are produced. The lens may be a fresnel lens used to fan-shape the light rays in a plane. The two fan-shaped rays intersect at line 9, precisely marking the planned puncture path for insertion of puncture needle 10. When the puncture needle is held at the planned angle of insertion, the needle reflects the additive mixed bright yellow light which is produced by the red and green laser rays. When the needle deviates from the planned angle, either the red or the green laser light is reflected by the needle. In this manner, deviation from the planned guide path is immediately indicated to the physician by the clear green or red illumination of the needle and correction can be made. As noted above, using such an apparatus the planned angle of insertion can be observed strictly with a tolerance of ±1°.

Figure 2:
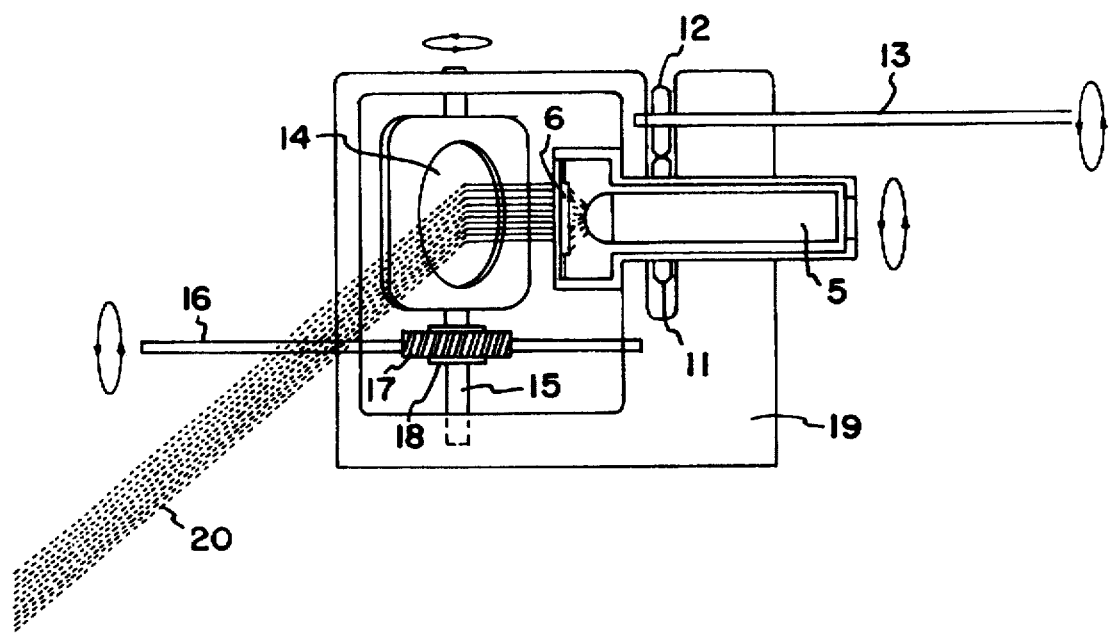
FIG. 2 represents a cross-sectional view of a laser light source used in accordance with an embodiment of the invention.

FIG. 2 shows a cross-sectional view of an exemplary laser-light guidance system. A laser diode module 5 is arranged rotatably around its axis and is coupled to a toothed wheel pair 11 and 12. By inducing an angular rotation about an angular position axis 13 the laser diode module 5 can be rotated around its axis. A cylindrical lens assembly 6 is connected to the laser diode module 5. The connection of cylindrical lens 6 with laser diode module 5 has a sufficient torsional strength such that the angular position of the fan-shaped laser ray can be adjusted by actuating rotation along the angular position axis 13.

A light ray 20 is emitted from the laser diode module 5, formed into a fan-shape by cylindrical lens 6 and reflected by a mirror 14. The mirror 14 is coated on its face (front surface) and is rotatable around a mirror axis 15. A worm wheel 17 is provided along rotational axis 16 and engages a toothed wheel 18 coupled to the mirror 14. The toothed wheel 18 is disposed so as to rotate about the mirror axis 15. For rotation of mirror 14 the worm wheel 17 catches the toothed wheel 18 so that the position of the mirror 14 may be adjusted by rotation about the rotational axis 16. In this manner, the mirror 14, and consequently the orientation of the outgoing light ray 20, can be adjusted. The above described rotation axis are arranged in friction bearings of a gear unit 19.

Figure 3:
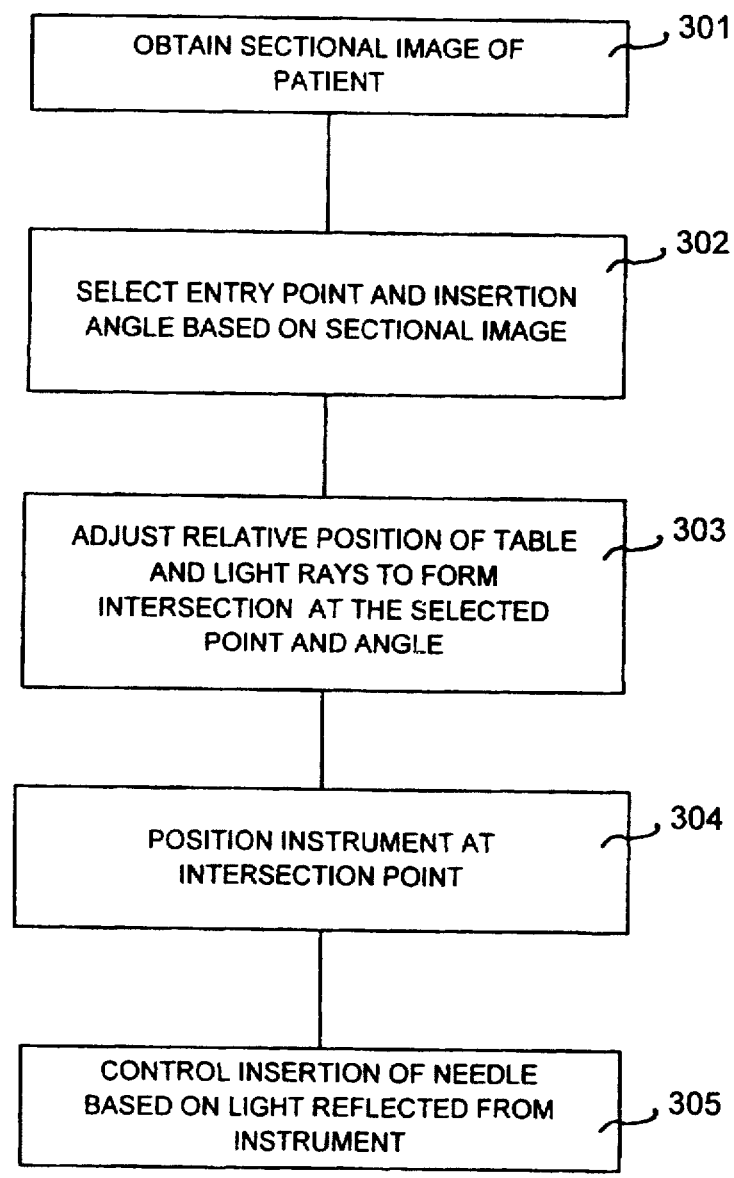
FIG. 3 is a flow diagram illustrating a process in accordance with an embodiment of the invention.

A method of precisely guiding a medical instrument using the above described embodiments of the apparatus is illustrated in FIG. 3. At step 301 one or more sectional images of a patients body are obtained, using for example, computer tomography or magnetic resonance imaging. These images may be used, for example, to localize a lesion inside the patient's body. Using a sectional image which shows the target point the physician determines the most favorable entry point and insertion angle according to the anatomic circumstances at step 302. Using the selected entry point and insertion angle, at step 303 the relative position of the table and the two light rays are adjusted to align the intersection of the light rays along the desired insertion path. This may be accomplished by manually adjusting the angular position of the laser diode module 5 by rotating the system about axis 13 and the angular position of mirror 14 by rotating the worm gear 17 about axis 16. By appropriately adjusting the laser guidance systems 3 and 4 in this manner, the intersection point can be set with extreme precision.

Once the intersection of the two light rays is appropriately adjusted, the medical instrument, such as the puncture needle 10 illustrated in FIG. 1, is positioned at the marked puncture path at step 304 by placing the needle tip on the patient's body at the intersecting point of the laser rays. Light reflected from the medical instrument is then visually inspected by the physician and used to obtain the desired angular position. In the above example of red and green laser light, the instrument is position so as to obtain a bright yellow reflection along the entire length of the needle. The needle is then inserted into the patient at marked angular position using the reflected light as a guide at step 305. If necessary, needle position inside the patient's body can be controlled by means of a new tomogram after insertion.

In the above example, an insertion angle is selected by the physician and is used to manually adjust the laser rays until the angle of intersection corresponds to the desired insertion angle. In an alternative embodiment, the entry point and insertion angle may be selected directly by marking the desired point and angle on the screen of the computer tomographic or magnetic resonance imaging device while viewing the image. Using the data input via an interface with the screen, a computer may be used to calculate the necessary relative positions of table 1 and laser light guidance system 3, 4 as well as the appropriate directions and angular position of the planes of laser rays 7, 8. The calculated coordinates may then be used to generate control commands for adjusting table 1 and laser guidance system 3, 4 in a manner that these laser rays 7, 8 appear on the planned entry point and marks the planned insertion angle. Control commands may be provided to an appropriate device which impart a rotation about axis 13 and 16.

The foregoing description, which has been disclosed by way of the above examples and discussion, addresses embodiments of the present invention encompassing the principles of the present invention. The embodiments may be changed, modified and/or implemented using various arrangements. Those skilled in the art will readily recognize that these and various other modifications and changes may be made to the present invention without strictly following the exemplary embodiments and applications illustrated and described herein, and without departing from the true spirit and scope of the present invention which is set forth in the following claims.

What is claimed is:

1. A device for guiding a medical instrument for insertion into a body of a patient along a planned guide path at a planned angle of insertion, the device comprising:

a first source of electromagnetic radiation producing a first ray;

a second source of electromagnetic radiation producing a second ray;

wherein at least the first source is configured and arranged for rotatable adjustment of the first ray to provide an intersection of the first ray and the second ray along the planned guide path at the planned angle of insertion to mark the planned guide path, the first and second rays are visible light rays of different colors which mix at a point of intersection of the first and second rays to produce a third color when reflected by the medical instrument at the point of intersection.

2. A device as recited in claim 1, wherein the first and second ray are respectively formed into first and second fan-shaped rays, an intersection point of a plane of the first fan-shaped ray with a plane of the second fan-shaped ray forming the planned guide path.

3. A method of aligning a medical instrument for insertion into a body of a patient along a planned guide path, comprising the steps of:

producing a first visible light ray of a first color;

producing a second visible light ray of a second color;

intersecting the first and second visible light rays along the planned guide path at a planned angle of insertion to mix the first and second colors to form a third color, wherein at least the first ray is rotatably adjustable to produce the guide path at a planned point of intersection; and guiding the medical instrument along the guide path at the planned angle of insertion.

4. A method as recited in claim 3, wherein the medical instrument is aligned to a lesion in the body by intersecting the first and second rays so that the line of intersection points directly to the lesion.

5. A method as recited in claim 3, wherein the step of producing a first ray of electromagnetic radiation further comprises the step of shaping the first ray of electromagnetic radiation as a fan in a first plane, and shaping the second ray of electromagnetic radiation as a fan in a second plane, and the step of intersecting the first and second rays comprises the step of intersecting the first plane and the second plane to produce the guide path at the point of intersection of the first plane and the second plane.

6. A device for marking a planned guide path at a planned angle of insertion of a puncture needle, comprising first and second sources of electromagnetic radiation, the first and second sources producing first and second visible light rays, respectively, the first and second visible light rays having a first and a second color, respectively; wherein at least the first source is configured and adapted for rotatable adjustment of the first ray to provide an intersecting line of the first ray and the second ray along the planned guide path at the planned angle of insertion, the first and second colors mixing along the intersecting line to form a third color.

7. A device according to claim 6, wherein the sources of electromagnetic radiation produce the first and second rays each situated to produce first and second planes, the intersecting line of the first and second planes marking the planned guide path.

8. A device according to claim 7, wherein the first source of electromagnetic radiation comprises light having a wavelength of 635 nanometers and the second source of electromagnetic radiation comprises light having a wavelength of 532 nanometers.

9. A device according to claim 7, wherein the sources of electromagnetic radiation comprise diode lasers.

10. A device according to claim 7, wherein each source of electromagnetic radiation comprises a cylindrical lens for fan-shaping the first and second rays in respective planes.

11. A device according to claim 7, wherein a crossing angle of the rays ranges from 60° to 120°.

12. A device according to claim 11, wherein the crossing angle is substantially 90°.

13. Device according to claim 11, wherein each source of electromagnetic radiation comprise a fresnel lens for fan-shaping the first and second rays in respective planes.

14. Device according to claim 6, wherein the device consist of only non-magnetic material.

* * * * *